United States Patent
Feng et al.

(10) Patent No.: US 12,238,945 B2
(45) Date of Patent: Feb. 25, 2025

(54) DYNAMIC UREA BOND-BASED PASSIVATORS OF PEROVSKITE

(71) Applicant: THE UNIVERSITY OF HONG KONG, Hong Kong (HK)

(72) Inventors: Shien Ping Feng, Hong Kong (HK); Wei Ting Wang, Hong Kong (HK)

(73) Assignee: THE UNIVERSITY OF HONG KONG, Hong Kong (HK)

(*) Notice: Subject to any disclaimer, the term of this patent is extended or adjusted under 35 U.S.C. 154(b) by 0 days.

(21) Appl. No.: 18/272,356

(22) PCT Filed: Jan. 27, 2022

(86) PCT No.: PCT/CN2022/074284
§ 371 (c)(1),
(2) Date: Jul. 14, 2023

(87) PCT Pub. No.: WO2022/166750
PCT Pub. Date: Aug. 11, 2022

(65) Prior Publication Data
US 2024/0099037 A1  Mar. 21, 2024

Related U.S. Application Data

(60) Provisional application No. 63/145,026, filed on Feb. 3, 2021.

(51) Int. Cl.
| | |
|---|---|
| H10K 30/50 | (2023.01) |
| C07C 333/20 | (2006.01) |
| H10K 85/50 | (2023.01) |
| H10K 85/60 | (2023.01) |

(52) U.S. Cl.
CPC .......... *H10K 30/50* (2023.02); *C07C 333/20* (2013.01); *H10K 85/50* (2023.02); *H10K 85/60* (2023.02)

(58) Field of Classification Search
None
See application file for complete search history.

(56) References Cited

U.S. PATENT DOCUMENTS

| | | |
|---|---|---|
| 10,000,608 B2 | 6/2018 | Cheng |
| 2016/0320054 A1 | 2/2016 | Swander |
| 2017/0032762 A1 | 11/2017 | Smadi |
| 2019/0092898 A1 | 3/2019 | Cheng |

FOREIGN PATENT DOCUMENTS

CN  112133833 A * 12/2020  ......... H01L 51/0003

OTHER PUBLICATIONS

H. Lin et al., "Polyaromatic nanotweezers on semiconducting carbon nanotubes for the growth and interfacing of lead halide perovskite crystal grains in solar cells", Chemistry of Materials 32, p. 5125-5133 (Year: 2020).*
Machine translation of CN112133833A (Year: 2020).*
(Continued)

*Primary Examiner* — Ryan S Cannon
(74) *Attorney, Agent, or Firm* — Amin, Turocy & Watson, LLP

(57) ABSTRACT

Disclosed is a passivated perovskite structure containing a perovskite layer; and a hindered urea bond-based Lewis acid-base containing layer adjacent the perovskite layer. Also disclosed are solar cells containing the passivated perovskite structure.

18 Claims, 11 Drawing Sheets

(56) References Cited

OTHER PUBLICATIONS

Y. Lv, et al., "All-in-one deposition to synergistically manipulate perovskite growth for high-performance solar cell", Research 2763409 (Year: 2020).*

International Search Report an Written Opinion for International Application Serial No. PCT/CN2022/074284 mailed on Apr. 27, 2022, 9 pages.

* cited by examiner

DYNAMIC UREA BOND-BASED PASSIVATORS OF PEROVSKITE

CROSS REFERENCE TO RELATED APPLICATION

The present application claims the benefit of U.S. Provisional Patent Application No. 63/145,026 filed on Feb. 3, 2021, the entire content of which is incorporated by reference for all purpose.

FIELD OF INVENTION

Disclosed are passivated perovskite structures, methods of passivating perovskite structures and methods of making passivated perovskite structures, and solar cells containing the passivated perovskite structures.

BACKGROUND OF INVENTION

Organic-inorganic hybrid halide perovskites have been the most promising next-generation photovoltaic candidates because the state-of-the-art performance of single-junction solar cells has reached over 25% and is comparable to that of crystalline silicon. Further improvements in performance still require precise control of the trap state located at the surface and grain boundaries (GBs) of poly-crystalline perovskites; therefore, various defect-suppressing passivation strategies have been taken into consideration. Quaternary ammonium halides have been investigated to passivate the defects of perovskite by adjusting the molecular structures and the open-circuit-voltage deficit was reduced to 0.39 V. In another work, a thin layer of mechanically robust lead oxysalt fabricated on perovskite surface, which not only enhances chemical stability of perovskite but also greatly improves the device stability. Excess lead iodide has been doped into the perovskite precursor solution, the excess lead iodide suppresses charge recombination by the formation of I-type band alignment at the grain boundaries and on the surface. A thin layer of wide-bandgap perovskite halide was fabricated to effectively passivate the charge traps and produce a significant improvement of open-circuit voltage ($V_{oc}$) around 0.2 V. However, the poly-crystalline perovskites are sensitive to subtle changes in manufacturing and device storage conditions, such as hygroscopic dopants and atmospheric moisture. This causes difficulties in controlling the trap density for reproducible and predictable device performance and stability.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Rather, the sole purpose of this summary is to present some concepts of the invention in a simplified form as a prelude to the more detailed description that is presented hereinafter.

Perovskite solar cells (PSCs) are promising for next-generation solar energy harvesting. Further improvement of performance requires better control of ionic defects in the perovskite active layer. Passivation strategies have been widely studied to suppress defects by using ionic/coordinate bonds. However, the surface morphology and composition of perovskite are easily affected by environmental factors and may even produce more defects without additional healable passivation. This work reports a new dynamic passivation strategy based on our synthesized hindered urea bond-based Lewis acid-base (HUBLA) material. The introduction of dynamic covalent bond gives the material the ability to absorb moisture and then releases Lewis bases to heal the defects, which improves device performance up to 22.3% and sustains more than 85% power conversion efficiency (PCE) of perovskite solar cells after 3500 hours of storage under ambient conditions. This work opens a promising strategy for effective utilization of environmental humidity to passivate perovskite.

Disclosed herein are passivated perovskite structures including perovskite solar cells containing a perovskite layer; and a hindered urea bond-based Lewis acid-base containing layer adjacent the perovskite layer.

Also disclosed are methods of passivating a perovskite layer involving forming a hindered urea bond-based Lewis acid-base containing layer adjacent the perovskite layer.

To the accomplishment of the foregoing and related ends, the invention comprises the features hereinafter fully described and particularly pointed out in the claims. The following description and the annexed drawings set forth in detail certain illustrative aspects and implementations of the invention. These are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 12(a) Chemical structures of HUB and its dynamic reaction. FIG. 12(b) Polymerization reaction of poly(urethane-urea) elastomer. FIG. 12(c) Photographs of the self-healing experiment of HUB-based cross-linked poly(urethane-urea). FIG. 12(d)-(f) Illustration of the self-healing mechanism of HUB-based cross-linked poly(urethane-urea).

FIG. 13(a) Chemical reaction of preparing HUBLA. FIG. 13(b) Photographs showing the connection of two FAPbI$_3$ single crystals using HUBLA. FIG. 13(c) Reversible and hydrolysis reaction of HUBLA. FIG. 13(d) NMR characterizations of HUBLA in DMSO-$d_6$ and $D_2O$ within 60 min. FIG. 13(e) Concentration of HUB.

FIG. 14(a) Ionic interaction of HUBLA and perovskite on the surfaces and at the grain boundaries. FIG. 14(b) Hydrolysis reaction and passivation mechanism of HUBLA on perovskite. FTIR spectra of FIG. 14(c) pristine and FIG. 14(d) HUBLA-coated perovskite films within 12 days. FIG. 14(e) Steady-state PL and FIG. 14(f) TRPL of pristine and HUBLA-coated perovskite single crystals.

FIG. 15(a) Schematic device structure (ITO/$SnO_2$/perovskite/HUBLA/Spiro-OMeTAD/$MoO_x$/Ag).

FIG. 15(b) Best J-V curves of the control and HUBLA devices. FIG. 15(c) Statistic mapping of control and HUBLA devices. FIG. 15(d) Stability tests of pristine and HUBLA-modified perovskite solar cells stored under controlled ambient conditions.

FIG. 16(a) Electron- and FIG. 16(b) hole-only devices of pristine and HUBLA-coated perovskite films. Theoretical models of perovskite with molecular surface passivation of FIG. 16(c) tBEDA and FIG. 16(d) NH-AS. Density of states of the pristine perovskite and the perovskite coated with FIG. 16(e) tBEDA and FIG. 16(f) NH-AS.

DETAILED DESCRIPTION

Figure 1:
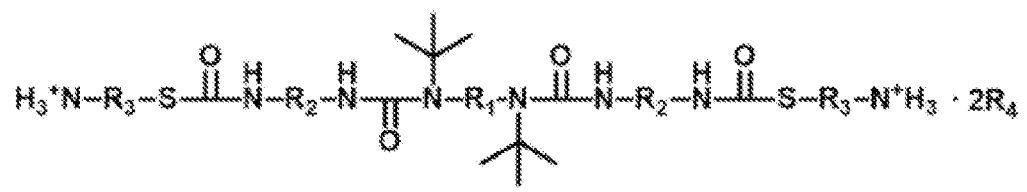
FIG. 1 depicts the chemical structure of HUBLA.

Perovskite solar cells (PSCs) are promising for next-generation solar energy harvesting. A PSC is a type of solar cell which includes a perovskite-structured compound, such as a hybrid organic-inorganic lead or tin halide-based material, as the light-harvesting active layer. Perovskite materials include, for example, methylammonium lead halides, formamidinium lead halides, mixed lead-tin halides, and all-inorganic cesium lead halides. Further improvement of performance requires better control of ionic defects in the perovskite active layer. Passivation strategies have been widely studied to suppress defects of perovskite by using ionic/coordinate bonds. However, the surface morphology and composition of perovskite are easily affected by environmental factors and may even produce more defects without additional healable passivation. This invention introduces a dynamic hindered urea bond-based Lewis acid-base (HUBLA) material as the passivator. In particular, the design of dynamic covalent bond gives the material the ability to absorb moisture and then releases Lewis bases to heal the defects, which improves device performance up to 22.3% and sustains more than 85% PCE of perovskite solar cells after 3500 hours of storage under ambient conditions. This work opens a promising strategy for effective utilization of environmental humidity to passivate perovskite.

Improvements in the performance of perovskite solar cells require precise control of the trap state located at the surface and grain boundaries (GBs) of poly-crystalline perovskites; therefore, various defect-suppressing passivation strategies have been taken into consideration. However, the poly-crystalline perovskites are sensitive to subtle changes in manufacturing and device storage conditions, such as hygroscopic dopants and atmospheric moisture. This causes difficulties in controlling the trap density for reproducible and predictable device performance and stability. To mitigate the instability issues aggravated in the presence of traps, developing environmental factor-triggerable materials is imperative to prevent moisture-induced degradation and heal the defects. This invention effectively solves the problem by developing a water-triggerable and self-healing Lewis acid (HUBLA) incorporating dynamic hindered urea bond (HUB) groups as hydrolyzed agents. In particular, HUBLA can be triggered by water to produce new Lewis base groups. As a result, HUBLA not only avoids moisture penetration but also produces new passivation agents triggered by environmental moisture, thereby boosting the performance of PSC and improving long-term device stability.

Highly reactive electrophiles can acquire electrons from water molecules, which is therefore a critical feature of moisture-triggerable material. Since electrophiles (e.g. iso-cyanates) are electron-deficient species, and are easily reacted with solvents (e.g. iso-propanol). Thus, a protective nucleophile is required to form reversible covalent bonds with electron-rich nucleophiles via the following equation:

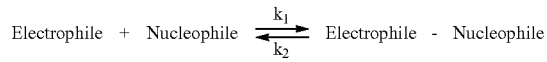

where $k_1$ and $k_2$ are rate constants of the forward and reverse reaction. To ensure the device stability and moisture-triggerable property, the two important criteria that must be met: first, both the forward and reverse reaction rate ($k_1$ and $k_2$) should be fast; second, the equilibrium must favor the formation of product ($k_1/k_2$ is large). It is a challenge for one chemical structure with both unique and contradictory dynamic properties.

A dynamic ester bond and malleable thermosets, in which metal catalysts were added to accelerate the transesterification reaction at high temperature, have been made. Afterward, various dynamic covalent bonds (DCBs) were developed. For instance, a lightly crosslinked polybutadiene becomes malleable with Grubb's catalyst, which promotes olefin metathesis. And poly(hexahydrotriazine)s can be depolymerized by acid and recycled. Compared with hydrogen bonds and coordinate bonds, one might predict that DCBs with higher bonding energy have greater hope for stable application in PSCs. However, the dissociation-association reaction in DCBs generally requires high temperature and catalyst, which do not align well with the operating conditions of PSCs.

Recently, room-temperature-processed and catalyst-free hindered urea bonds (HUBs) demonstrate excellent hydrolysable properties and additionally produce amine groups at room temperature via the following equation. Interestingly, the amine groups are considered as an effective Lewis base for healing the perovskite defects.

Hydrolysis reaction: $R_1NCO + H_2O \longrightarrow R_1NC(O)OH \longrightarrow R_1NH_2 + CO_2$ Under these circumstances, this work synthesized a water-triggerable and self-healing Lewis acid-base (HUBLA) material by incorporating dynamic HUB groups as hydrolyzed agents. In particular, HUBLA can be triggered by water to produce new Lewis base groups. As a result, HUBLA cannot only avoid moisture penetration but also produce new passivation agents trigged by environmental moisture, thereby boosting the performance of PSC and improving the long-term device stability. In addition, HUBLA exhibited the unique ability to crosslink and heal the interfaces of two perovskite crystals; this characteristic also helped to enhance the robustness of perovskite film. The resulting PSC showed a significant reduction in open-circuit voltage ($V_{oc}$) deficit and an improvement in power conversion efficiency (PCE). This study introduced an effective passivation material to heal perovskite, providing new insights into the use of moisture, which was previously considered to be detrimental, to prolong the service life and sustain the high-performance of PSCs.

The chemical structure of HUBLA is shown in FIG. 1. $R_1$ is selected from

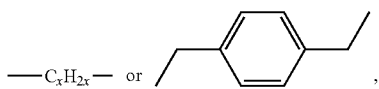

where x is selected from 1 to 5. $R_2$ is selected from

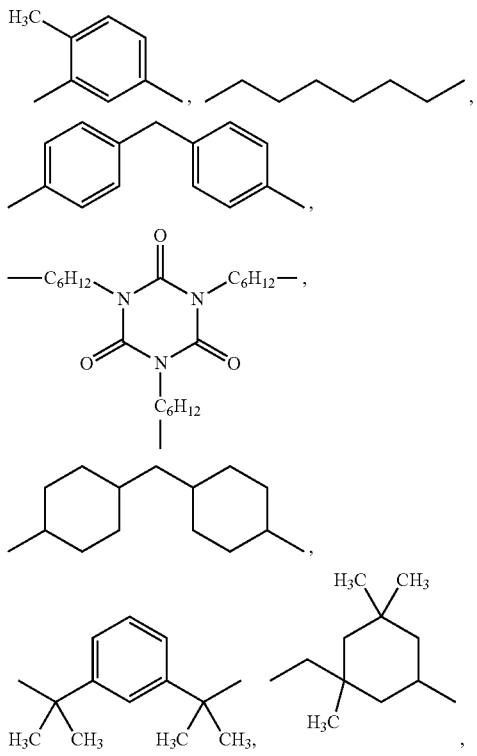

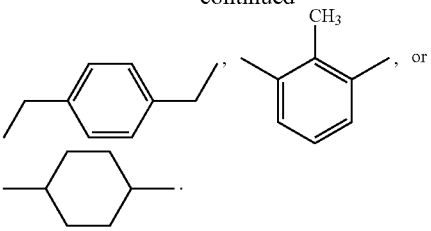

$R_3$ is selected from $-C_xH_{2x}-$, where x is selected from 1 to 5. $R_4$ is a halide selected from $Cl^-$, $Br^-$, $I^-$.

Figure 2:
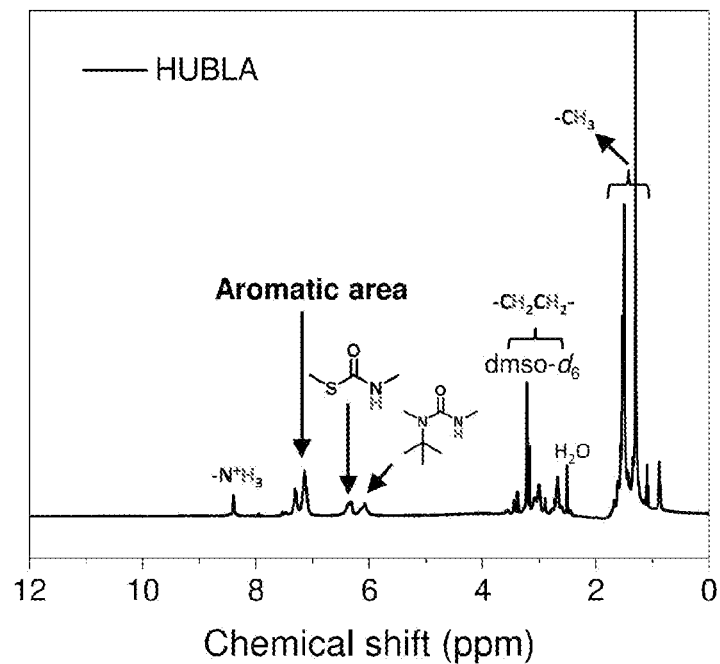
FIG. 2 depicts a $^1$H-NMR spectroscopy of HUBLA.

The chemical structure of HUBLA is characterized using nuclear magnetic resonance (NMR) spectroscopy. One example of HUBLA is shown in FIG. 2.

Figure 3:
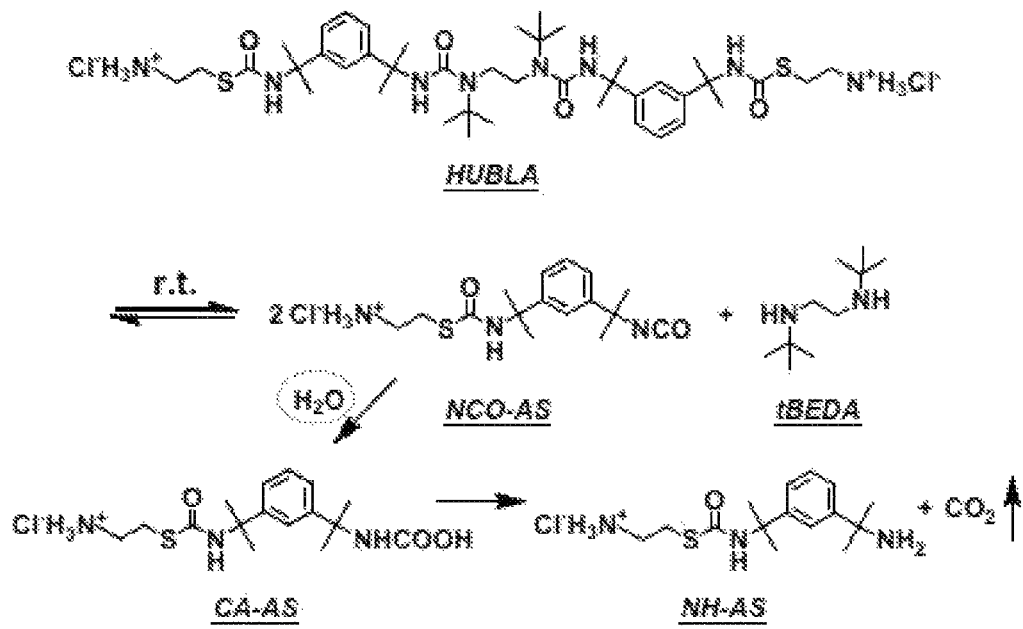
FIG. 3 depicts a chemical structural view of dynamic and hydrolysis reactions of HUBLA.

HUBLA undergoes a dynamic reaction and dissociated to NCO-terminated ammonium salt (NCO-AS) and N,N'-Di-tert-butylethylenediamine (tBEDA). The NCO-AS can absorb water molecules and produce the carbamic acid-terminated ammonium salt (CA-AS), which will further decompose into $NH_2$-terminated ammonium salt (NH-AS) and carbon dioxide, as shown in FIG. 3.

Figure 4:
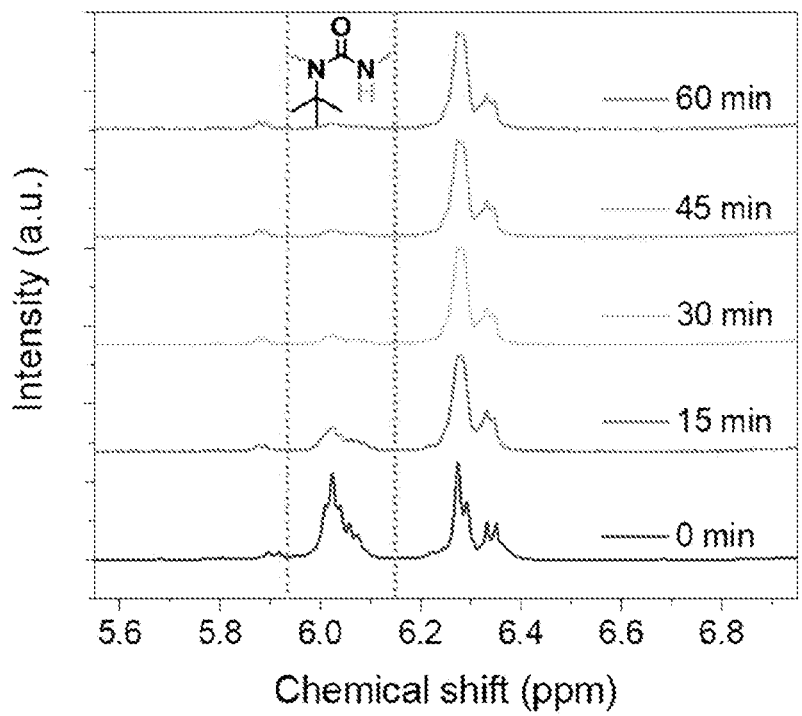
FIG. 4 depicts NMR characterization of hydrolysis reaction of HUBLA.

A 15% (v %) deuterium oxide ($D_2O$) is added into the HUBLA/DMSO-d6 mixture for the NMR characterization as shown in FIG. 4, the peak intensity of HUB at ~6.02 ppm is dropped rapidly to 27.5% after 15 min and to 5.5% within one hour.

Figure 5:
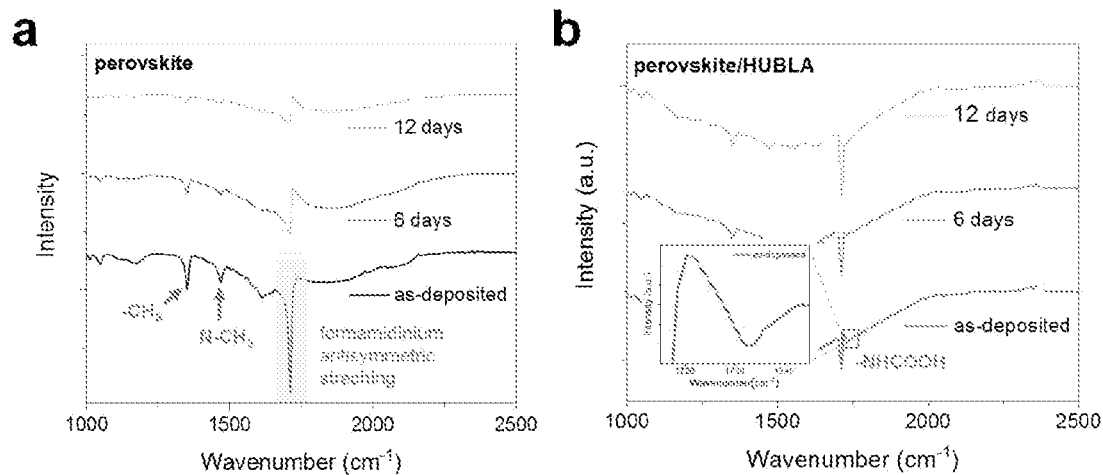
FIG. 5 depicts ATR-FTIR spectra of FIG. 5(a) pristine perovskite film and FIG. 5(b) perovskite/HUBLA film.

The Attenuated total reflectance-Fourier transform infrared (ATR-FTIR) spectra of pristine and HUBLA-modified perovskite films are measured during 12 days, as shown in FIG. 5. The characteristic peaks at ~1350 cm$^{-1}$, ~1469 cm$^{-1}$ and ~1710 cm$^{-1}$ can be assigned to the vibration of $-CH_3$ and $N-CH_3$, and formamidinium antisymmetric stretching, respectively. As seen in FIG. 5a, the intensity of these peaks greatly decreased after 12 days, indicating the decomposition of $FAPbI_3$ (perovskite) crystal structure with the possibly formation of intermediate compounds. On the contrary, these characteristic peaks of the HUBLA-coated perovskite film still maintained prominent intensity after 12 days, verifying the protective capability of HUBLA, as shown in FIG. 5b. Note that, the small peak at 1734 cm$^{-1}$ in the insert figure can be assigned to the carbamic acid group (—NHCOOH from HUBLA), which is absent in the pristine perovskite; it is the functional group of CA-AS and a strong evidence for the hydrolysis of HUBLA.

Figure 6:
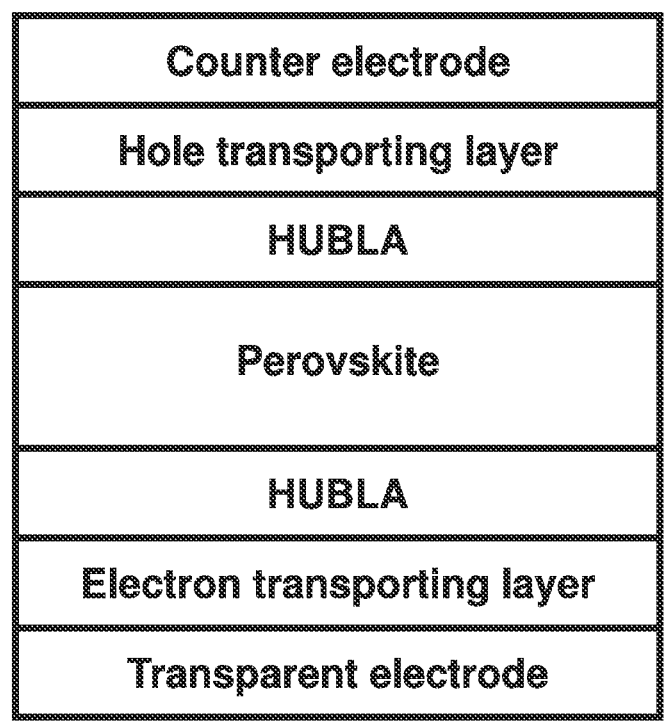
FIG. 6 depicts the structure of a conventional perovskite solar cell.

Then, HUBLA is used as the passivation material of a perovskite solar cell, and is utilized on the top and/or at the bottom of perovskite layer, as shown in FIG. 6. Where the transparent electrode is selected from fluorine-doped tin oxide or indium tin oxide; the electron transporting layer is selected from mesoporous titanium dioxide, titanium dioxide, tin oxide, zinc oxide, $C_{60}$, phenyl-C61-butyric acid methyl ester, phenyl-C71-butyric acid methyl ester; the perovskite layer is $FA_xMA_yCs_{1-x-y}Pb_zSn_{1-z}I_mBr_nCl_{3-m-n}$, and FA is the formamidinium, MA is the methylammonium, Cs is the cesium, Pb is the lead, Sn is the tin, I is the iodide, Br is the bromide, Cl is the chloride, x, y, z is between 0 to 1, m+n is between 0 to 3; hole transporting layer is selected from 2,2',7,7'-tetrakis-9,9'-spirobifluorene, poly[bis(4-phenyl)(2,5,6-trimethylphenyl)amine mixed with lithium bis(trifluoromethanesulfonyl)imide, 4-tertbutylpyridine, chlorobenzene (CB) or toluene; the counter electrode is selected from gold, silver, copper or with a thin layer of molybdenum oxide.

Figure 7:
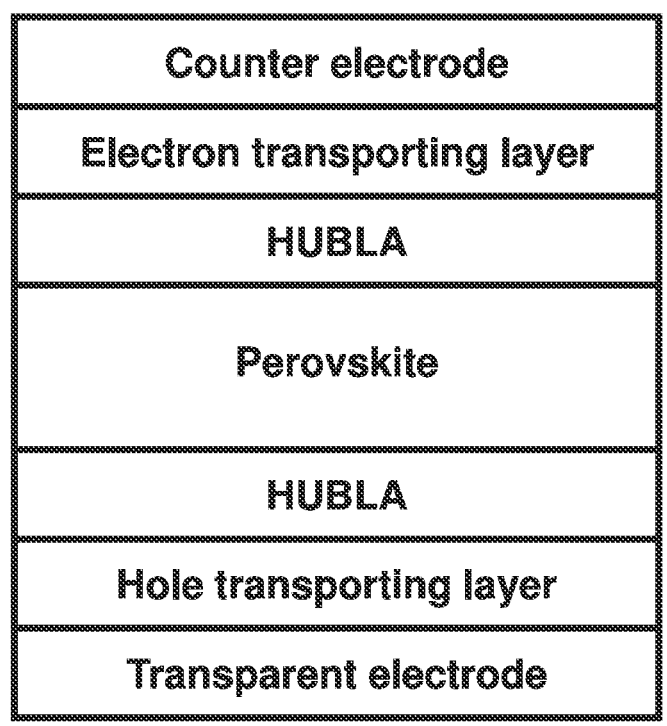
FIG. 7 depicts a structure of inverted perovskite solar cell.

HUBLA is also used as the passivation material of inverted perovskite solar cell, and is utilized on the top and/or at the bottom of perovskite layer in conventional photovoltaics, as shown in FIG. 7. Where the transparent electrode is selected from fluorine-doped tin oxide or indium tin oxide; hole transporting layer is selected from poly(3,4-ethylenedioxythiophene) polystyrene sulfonate, nickel oxide, poly[bis(4-phenyl)(2,5,6-trimethylphenyl)amine; the perovskite layer is $FA_xMA_yCs_{1-x-y}Pb_zSn_{1-z}I_mBr_nCl_{3-m-n}$, and FA is the formamidinium, MA is the methylammonium, Cs is the cesium, Pb is the lead, Sn is the tin, I is the iodide, Br is the bromide, Cl is the chloride, x, y, z is between 0 to 1, m+n is between 0 to 3; the electron transporting layer is selected from titanium dioxide, tin oxide, zinc oxide, $C_{60}$, phenyl-C61-butyric acid methyl ester, phenyl-C71-butyric acid methyl ester; the counter electrode is selected from aluminium, gold, silver, copper or with a thin layer of bathocuproine, polyethylenimine, or Poly(9,9-bis(3'-(N,N-dimethyl)-N-ethylammoinium-propyl-2,7-fluorene)-alt-2,7-(9,9-dioctylfluorene))dibromide.

The passivated perovskite structure has a HUBLA containing layer having a thickness sufficient to function as a passivation material. In one embodiment, the HUBLA containing layer has a thickness from 0.1 nm to 25 nm. In another embodiment, the HUBLA containing layer has a thickness from 0.2 nm to 10 nm.

The passivated perovskite structure has a HUBLA containing layer comprises a HUBLA in a concentration sufficient to function as a passivation material. In one embodiment, HUBLA containing layer comprises a HUBLA in a concentration of $0.01 \times 10^{-3}$ to $5 \times 10-2$ mg m$^{-2}$. In another embodiment, HUBLA containing layer comprises a HUBLA in a concentration of $0.05 \times 10^{-3}$ to $1 \times 10^{-2}$ mg m$^{-2}$.

Figure 8:
FIG. 8 depicts a conventional perovskite solar cell with a structure of ITO/SnO$_2$/perovskite/Spiro-OMeTAD/MoO$_x$/Ag.

Indium tin oxide (ITO)-coated glass substrate was cleaned by sequential sonication in deionized water, acetone, and isopropanol (IPA), then treating with ultraviolet ozone for 10 min after being dried with an air gun. Following this, $SnO_2$ nanoparticles (2.67%, diluted by deionized water) was spun onto the above substrate at 5,000 rpm for 30 sec, sequentially. And the film was annealed in ambient air at 150° C. for 30 min. For the perovskite deposition, the perovskite precursor solution was prepared according to the literature and optimized. Then the above solution was deposited onto the freshly prepared substrate using a two-step spin-coating method with 1,000 rpm for 10 sec and 5,000 rpm for 20 sec. During the second step, 100 µL of chlorobenzene (CB) was poured on the precursor film 10 sec prior to the end of spin and the film was then annealed at 100° C. for 30 min in a nitrogen-filled glove box. For the target device, HUBLA (0.03-0.2 mg mL$^{-1}$ in IPA) was spun onto the perovskite film. After that, the hole-transporting material (HTM) was deposited onto perovskite film at a spin rate of 4,000 rpm for 30 sec. Here, spiro-OMeTAD was selected as a HTM and dissolved in 1 mL of CB solution which contains 72.3 mg of spiro-OMeTAD, 18 µL of LiTFSI solution (520 mg mL$^{-1}$ in acetonitrile) and 30 µL of 4-tertbutylpyridine. The above film was then left overnight under controlled ambient conditions. Finally, molybdenum(VI) oxide ($MoO_x$) powder and silver (Ag) were thermally evaporated to fabricate the n-i-p cell. The structure of another perovskite solar cell is shown in FIG. 8.

Figure 9:
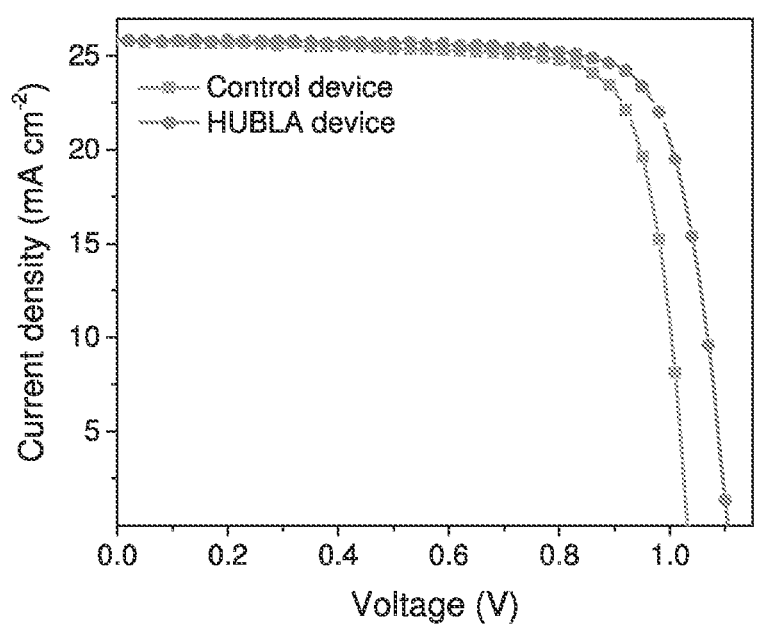
FIG. 9 depicts graphically a solar cell performance of control and HUBLA devices.

Control devices (ITO/$SnO_2$/perovskite/spiro-OMeTAD/ $MoO_x$/Ag) and HUBLA devices (ITO/$SnO_2$/perovskite/ HUBLA/spiro-OMeTAD/$MoO_x$/Ag) are fabricated and their performances are collected in FIG. 9. The highest Power conversion efficiency (PCE) in HUBLA device reached 22.3% with $J_{sc}$ of 25.85 mA cm$^{-2}$, $V_{oc}$ of 1.10 V and fill factor (FF) of 78.41%, while that of control device is 20.87%, with short-circuit current density ($J_{sc}$) of 25.84 mA cm$^2$, $V_{oc}$ of 1.03 V and fill factor of 78.43%. The increase in PCE was mainly originated from the $V_{oc}$ because HUBLA effectively passivated the perovskite films.

Figure 10:
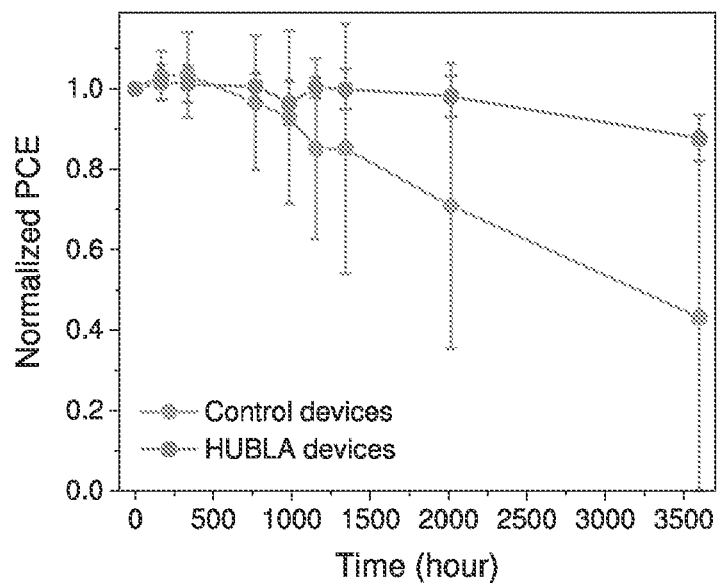
FIG. 10 depicts graphically a stability test of control and HUBLA devices.

In the stability test, the control and HUBLA devices are stored under ambient conditions (relative humidity (RH): ~30%) over 3500 hours (FIG. 10). The normalized PCE results show that the HUBLA device retained nearly 85% of the original performance, while that of the control device quickly dropped to 40%. The deviation in PCE of HUBLA devices is smaller than that of the control devices and stay around 10% after 3500 hours, while the deviation in PCE of the control devices is over 80%.

Figure 11:
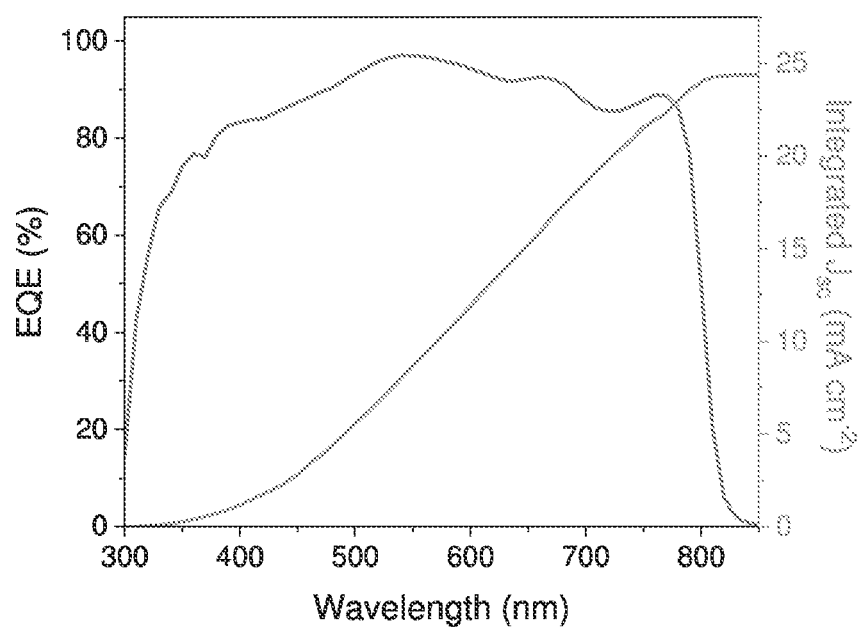
FIG. 11 depicts graphically an external quantum efficiency (EQE) of HUBLA device.

In addition, the external quantum efficiency (EQE) of HUBLA-modified device is shown in FIG. 11, of which the integrated current density well fits with the $J_{sc}$ data in J-V measurement.

Figure 12:
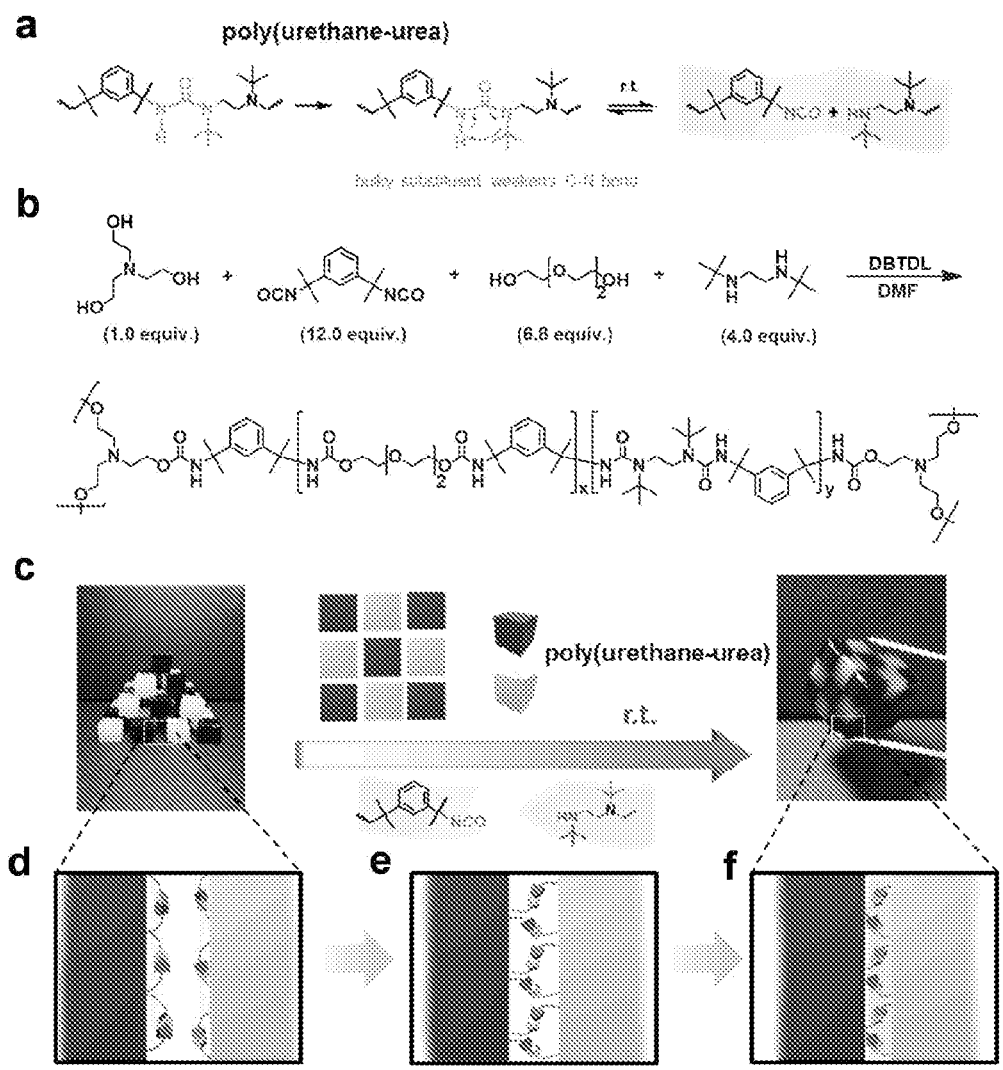
FIG. 12 depicts a dynamic reaction of hindered urea bonds (HUBs) and self-healing of Rubik's cube.

Before designing the passivator, a brief introduction to DCB is provided here. The dynamic behavior of the hindered urea bond originated from the non-coplanarity of the amide bond (FIG. 12), which was disturbed by the introduction of the bulky tert-butyl structure and thus enabled the dissociation-association reaction under room temperature (FIG. 12a). To illustrate the dynamic chemistry, a HUB-based poly(urea-urethane) elastomer (FIG. 12b) was prepared and its self-healing capability was demonstrated. In particular, triethanolamine (TEA), 1,3-bis(2-isocyanato-2-propyl)benzene (TMXDI), tri(ethylene glycol) (TEG), and tert-butylethylenediamine (tBEDA) were mixed and cured under room temperature to form the elastomer. To clearly demonstrate the self-rejoining property of elastomer, sixteen elastomer cubes (5×5×5 mm$^3$; poly(urethane-urea)) were dyed with black color while another sixteen cubes were white, as shown in FIG. 12c. Afterward, the permanently cross-linked elastomer cubes were rejoined to build a Rubik's Cube under room temperature after 24 hours of healing. The self-rejoining properties could be attributed to the dynamic reaction of HUBs, which underwent a dissociation-association reaction (the equilibrium reaction between HUB, isocyanate and hindered amine) at the interface, as shown in FIG. 12d to 12f. Initially, the HUB existing at the interfaces (FIG. 12d) dissociated at the surface of white and black cubes (FIG. 12e), and the isocyanate and hindered amine groups at different surfaces reacted and formed HUB again (FIG. 12f) when the two surfaces were close enough. After 24 hours, the interfacial cross-linking was strong enough to impart sufficient mechanical strength.

Figure 13:
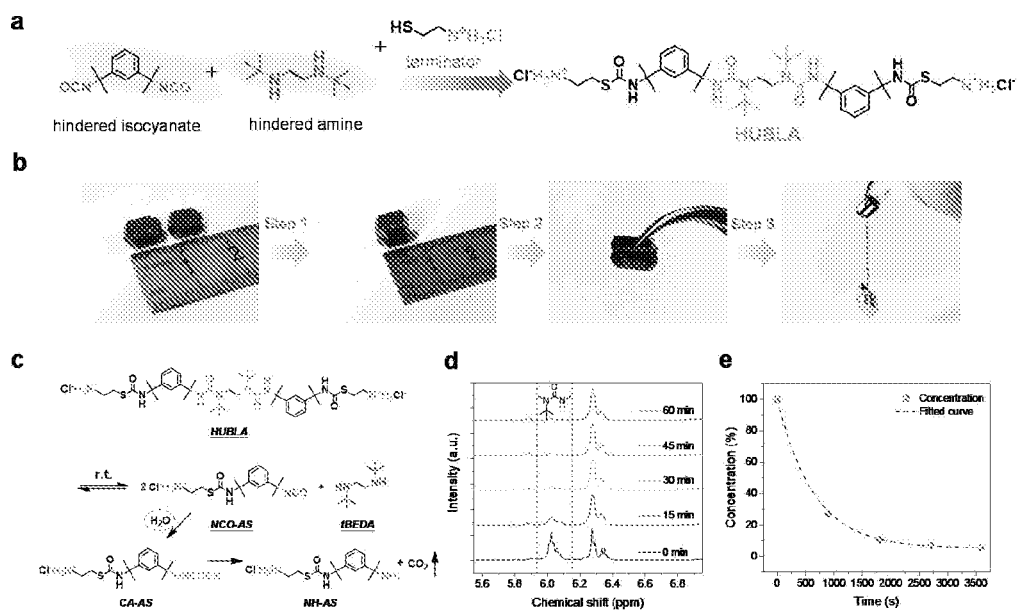
FIG. 13 depicts chemical structure, dynamicity and hydrolytic degradation of HUBLA.

To utilize the HUB moiety as a passivator for perovskite film, the chemical structure of the elastomer should be simplified and redesigned. First, we removed the toughener (TEG) and crosslinker (TEA) without passivation effects and only used tBEDA and TMXDI to produce the HUB bond. Further, the HUB-based structure was terminated with cysteamine hydrochloride, of which the ammonium chloride was considered as Lewis acid-base with the ability to heal both cationic and anionic defects of perovskite, as shown in FIG. 13a. HUBLA was synthesized via a one-pot reaction, and its chemical structure was then characterized by nuclear magnetic resonance spectroscopy (NMR, FIG. 2). Noted that, in contrast to polymers, small molecules generally do not have the ability to bond two surfaces. Interestingly, we found that HUB-based molecule can stick two FAPbI$_3$ single crystals, as shown in FIG. 13b, and this phenomenon can hereby demonstrate the dynamic reaction of HUBLA. In particular, HUBLA was coated (dissolved in iso-propanol) on one side of the FAPbI$_3$ single crystals and dried. One FAPbI$_3$ single crystal was covered onto the HUBLA-coated FAPbI$_3$ single crystal, and then the two crystals were stuck each other and kept under room temperature. After healing for 24 hours, the two single crystals exhibited strong bonding force to each other, and could lift a 5-gram weight, evidencing that HUBLA exhibited strong interactions between the two perovskite single crystals. The stickiness can be explained by the dissociation-association reaction of HUBLA at the interface to form cross-linked structures. The strong interaction between HUBLA and perovskite also imply that HUBLA can provide good protection on perovskite grain boundaries. The penetration of water molecules can be effectively prevented because the ammonia group of HUBLA formed a strong ionic interaction with the perovskite surface, while the grain boundaries of pristine perovskite or the spiro-OMeTAD-filled perovskite have gaps that allow penetration of water and hygroscopic dopants.

In this work, the most significant property of HUBLA was the generation of water-sensitive groups during the dissociation-association reaction, which not only absorbed humidity but also produced effective passivation agents for perovskite. To demonstrate the hydrolysis (water-sensitivity) property of HUBLA, the reaction mechanism was shown in FIG. 13c and was quantitatively monitored by NMR spectra (FIG. 13d). In particular, HUBLA underwent a dynamic reaction and dissociated to NCO-terminated ammonium salt (NCO-AS) and tBEDA. The NCO-AS can absorb water molecules and produce the carbamic acid-terminated ammonium salt (CA-AS), which will further decompose into NH$_2$-terminated ammonium salt (NH-AS) and carbon dioxide. A 15% (v %) D$_2$O was added into the HUBLA/DMSO-d$_6$ mixture for the NMR characterization as shown in FIG. 13d, the peak intensity of HUB around 6.02 ppm was dropped rapidly to 27.5% after 15 min and to 5.5% within one hour. The hydrolysis ratio of HUB was calculated and summarized in FIG. 13e. The HUBLA showed a remarkably enhanced hydrolytic degradation of the hindered urea bond (94.5%) compared to structures not containing the HUBLA; the faster hydrolytic behavior is attributed to the incorporation of bulky substituents in TMXDI, which disturbs the orbital coplanarity of the amide bonds and diminishes the conjugation effect. Here, the hydrolysis rate can be fitted by the equation below with a reaction rate coefficient of 1/644.7 s$^{-1}$.

$$\text{Hydrolysis rate} = \left(5.2 + 94.8 e^{-\frac{t}{644.7}}\right) \times 100\%$$

Figure 14:
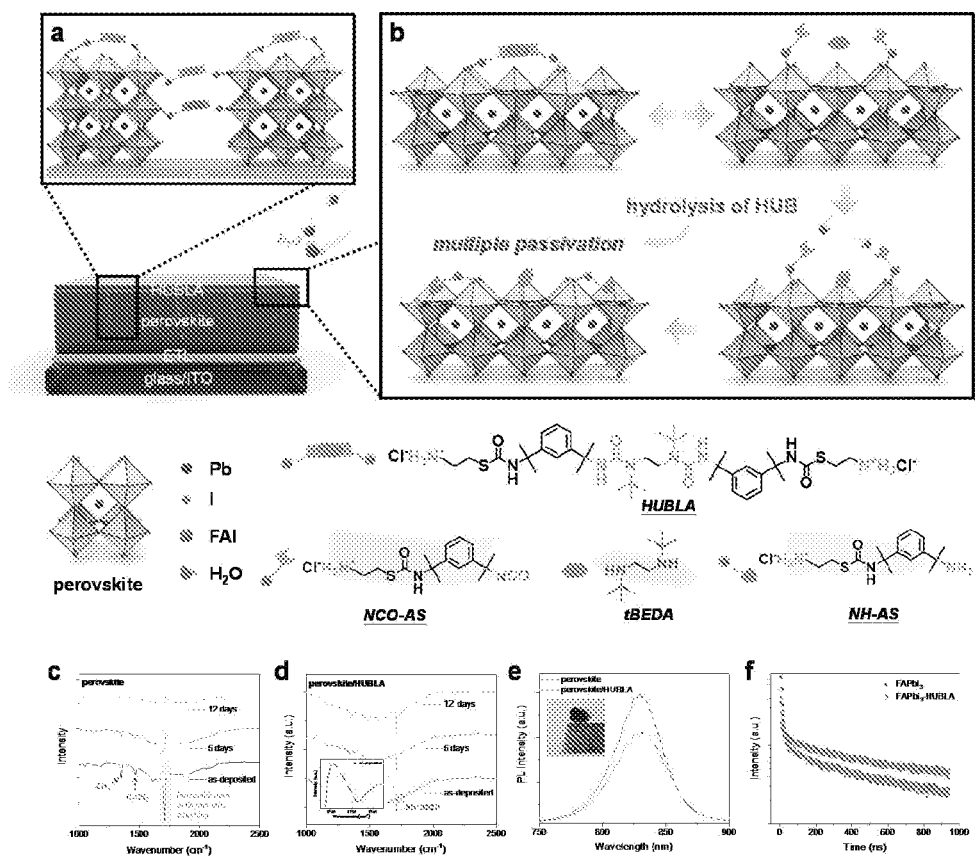
FIG. 14 depicts protection and passivation mechanism of HUBLA on perovskite films.

Based on the above analysis, we hypothesized that the protection and passivation mechanism of HUBLA on perovskite film proceeds through two pathways, as shown in FIGS. 14a and 14b. First, HUBLA with ammonium end group can interact with the unpaired lead vacancy (V$_{Pb}$) on the surfaces and grain boundaries via the ionic interaction. Second, HUBLA provided a multiple passivation strategy attributed to the room-temperature-reversible HUB. As shown in FIG. 14b, HUBLA underwent a dissociation-association reaction and the isocyanate group had the ability to absorb one water molecule when moisture penetrated through the transporting layer and electrode (upper two figures in FIG. 14b). The isocyanate quickly reacted with water to yield carbamic acid, and then decomposed to an amine group (blue pentagon) and released one carbon dioxide. The decomposition and hydrolysis of HUBLA can release tBEDA and NH-AS, of which the NH and NH$_2$ groups can further interact with the iodine vacancy (V$_I$) to heal the defects (lower two figures in FIG. 14b). To verify the protection and passivation effect, the HUBLA was coated on FAPbI$_3$ and tested with attenuated total reflection Fourier-transform infrared spectroscopy (ATR-FTIR), steady-state photoluminescence spectroscopy (PL) and time-resolved photoluminescence spectroscopy (TRPL). The ATR-FTIR spectra of pristine and HUBLA-modified perovskite films were measured during 12 days, as shown in FIGS. 14c and 14d, respectively. The characteristic peaks at 1350 cm$^{-1}$, 1469 cm$^{-1}$ and 1710 cm$^{-1}$ can be assigned to the vibration of —CH$_3$ and N—CH$_3$, and formamidinium antisymmetric stretching, respectively. As seen in FIG. 14c, the intensity of these peaks greatly decreased after 12 days, indicating the decomposition of FAPbI$_3$ crystal structure with the possibly formation of intermediate compounds. On the contrary, these characteristic peaks of the HUBLA-coated perovskite film still maintained prominent intensity after 12 days, verifying the protective capability of HUBLA. Note that, the small peak at 1734 cm$^{-1}$ in the insert figure can be assigned to the carbamic acid group (—NHCOOH from HUBLA), which is absent in the pristine perovskite; it is the functional group of CA-AS and a strong evidence for the hydrolysis of HUBLA. To verify the passivation effect of HUBLA, the PL and TRPL spectra of pristine and HUBLA-modified FAPbI$_3$ single crystals were measured, as shown in FIGS. 14e and 14f. The results indicated that the HUBLA-modified single crystal has a higher PL intensity with a longer lifetime, demonstrating that HUBLA can effectively decrease the carrier defect states and bimolecular radiative recombination of FAPbI$_3$ single crystals.

Figure 15:
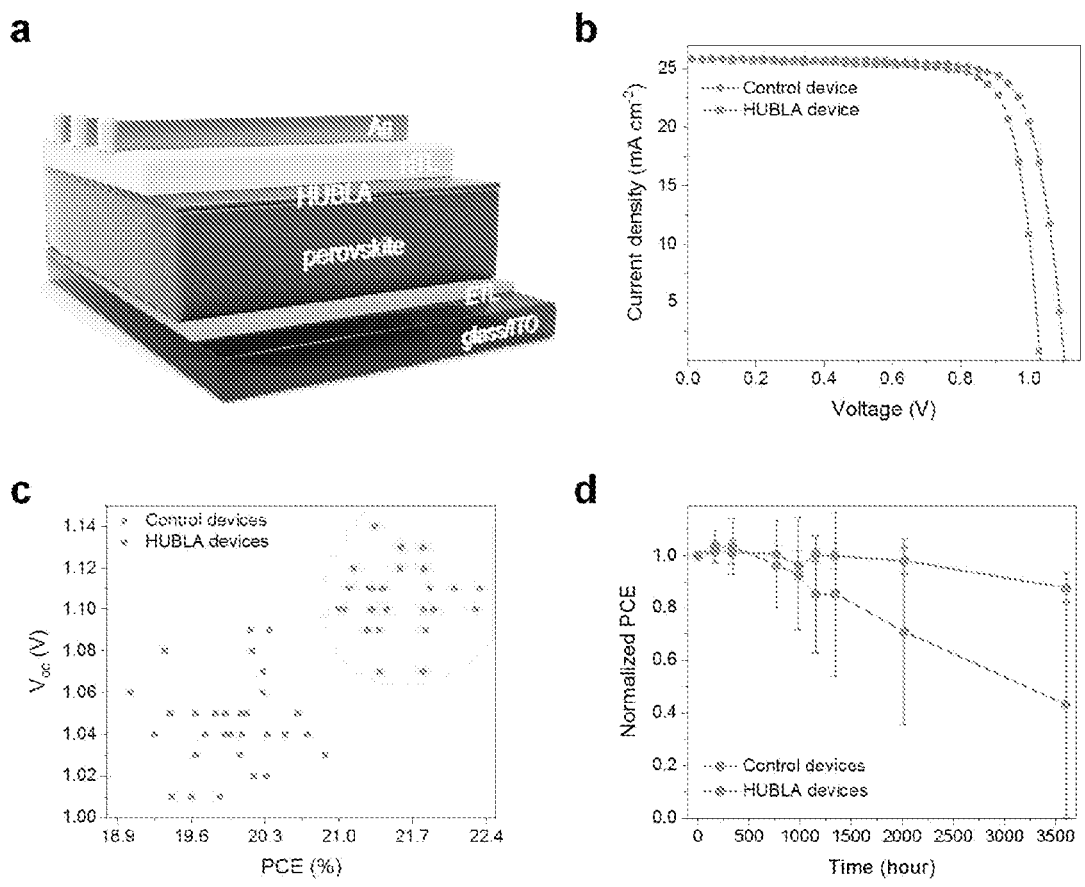
FIG. 15 depicts performance and stability of perovskite photovoltaics.

Afterward, control devices (ITO/SnO$_2$/perovskite/spiro-OMeTAD/MoO$_x$/Ag) and HUBLA devices (ITO/SnO$_2$/perovskite/HUBLA/spiro-OMeTAD/MoO$_x$/Ag) were fabricated utilizing SnO$_2$ and spiro-OMeTAD as electron transporting layer (ETL) and hole transporting layer, respectively, and their device performance and stability were compared and summarized in FIG. 15. The highest PCE in HUBLA device reached 22.3% with J$_{sc}$ of 25.85 mA cm$^{-2}$, V$_{oc}$ of 1.10 V and fill factor of 78.41%, while that of control device is 20.87%, with J$_{sc}$ of 25.84 mA cm$^{-2}$, V$_{oc}$ of 1.03 V and fill factor of 78.43%, as summarized in Table 1.

TABLE 1

Summary of photovoltaic parameters of the perovskite solar cell.

| PSC[a)] | J$_{sc}$ (mA cm$^{-2}$) | V$_{oc}$ (V) | FF (%) | PCE (%) |
|---|---|---|---|---|
| Control | 25.84 | 1.03 | 78.43 | 20.87 |
|  | (25.47) | (1.05) | (75.12) | (19.99) |
| HUBLA | 25.85 | 1.10 | 78.41 | 22.30 |
|  | (25.58) | (1.11) | (76.15) | (21.47) |

[a)]The brackets indicate the average values of thirty PSCs.

To further analyze reproducibility, thirty control and thirty HUBLA devices were fabricated and their PCE versus V$_{oc}$ were collected in FIG. 15c. The red points for the HUBLA devices showed a significant improvement as compared to the gray points of the control devices; the PCE and V$_{oc}$ of HUBLA devices achieved an average 7.4% and 5.7% improvement over the respective control device values. The increase in PCE was mainly originated from the V$_{oc}$ because HUBLA effectively passivated the perovskite films. In the stability test, the control and HUBLA devices were stored under ambient conditions (relative humidity (RH): ~30%) over 3500 hours (FIG. 15d). The normalized PCE results showed that the HUBLA device retained nearly 85% of the original performance, while that of the control device quickly dropped to 40%. The deviation in PCE of HUBLA devices was smaller than that of the control devices and stayed around 10% after 3500 hours, while the deviation in PCE of the control devices was over 80%. The stability test supported our proposed mechanism that HUBLA can absorb environmental moisture and thus protect perovskite films.

Figure 16:
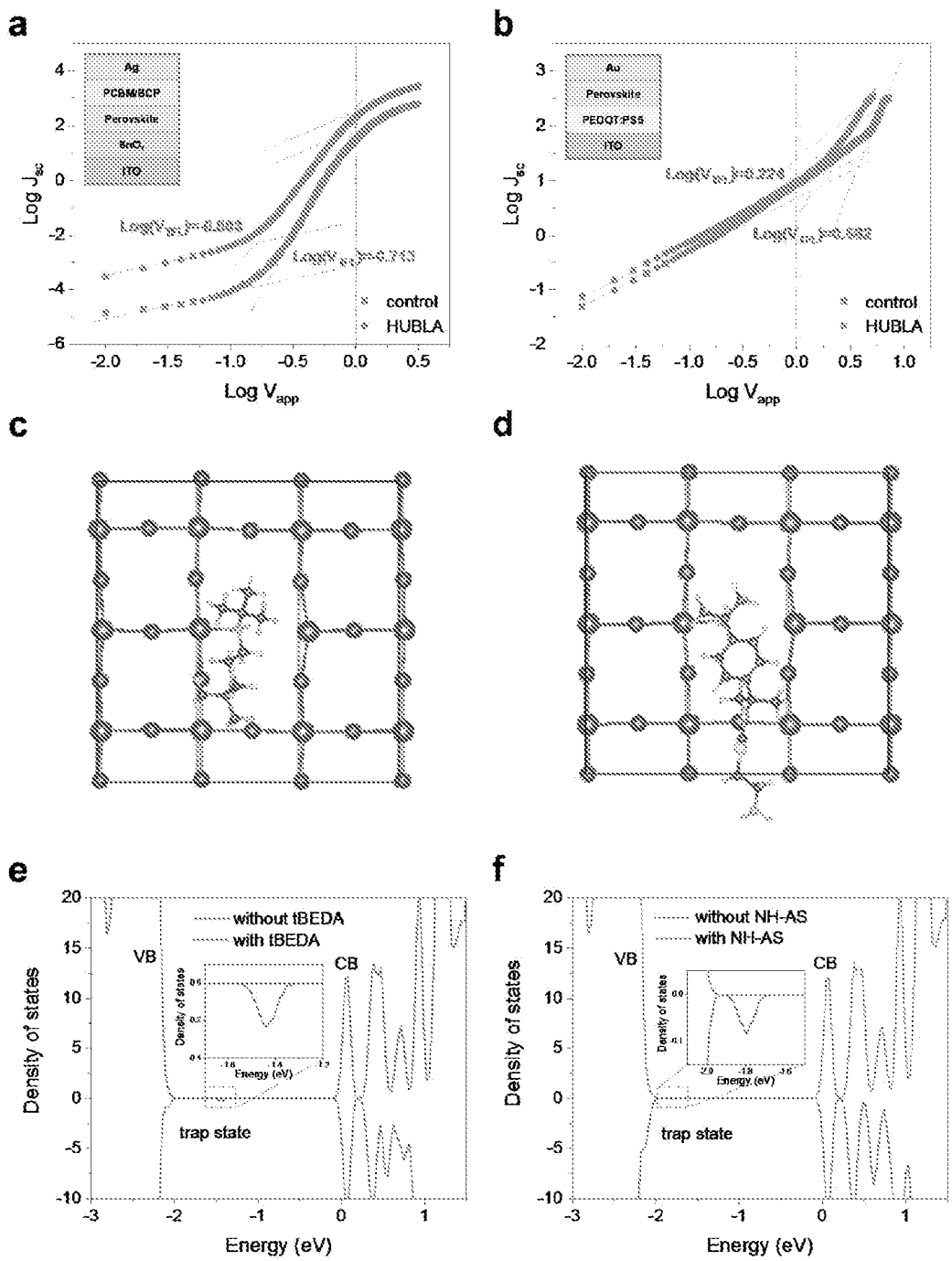
FIG. 16 depicts defects analysis and theoretical calculations.

Many factors may affect the device performance, including perovskite surface morphology, crystallinity, trap density, etc. Therefore, top-view scanning electron microscope (SEM), X-ray diffraction analysis (XRD) and space-charge limited current (SCLC) of pristine and HUBLA-modified perovskite films should be analyzed. The top-view SEM images indicated that no obvious difference could be identified between pristine and HUBLA-modified perovskite films, demonstrated the surface morphology changes did not contribute much to the performance. The XRD spectra both demonstrated similar peak intensities. Therefore, we can conclude that the improved PSC performance mainly comes from the reduction of trap density. For the electron- and hole-only devices as shown in FIGS. 16a and 16b, the trap density can be calculated by the following equation:

$$V_{TFL} = \frac{en_t d^t}{2\varepsilon\varepsilon_0}$$

where e is the electric charge, $n_t$ is the trap density, d is the thickness of perovskite (600 nm), $\varepsilon$ is the dielectric constant of perovskite, and $\varepsilon_0$ is the vacuum permittivity. In the results of electron-only devices, the control device showed a $V_{TFL}$ of 0.19 V and trap density of $2.88\times10^{15}$ cm$^{-3}$, and the HUBLA-modified device had lower $V_{TFL}$ of 0.16 V and trap density of $2.43\times10^{15}$ cm$^{-3}$. In the results of hole-only devices, the control device showed a $V_{TFL}$ of 3.82 V and trap density of $5.80\times10^{16}$ cm$^{-3}$, while HUBLA-modified device had a lower $V_{TFL}$ of 1.67 V and trap density of $2.54\times10^{16}$ cm$^{-3}$. The results evidenced that both electron- and hole-only devices modified by HUBLA can improve the trap densities.

As quaternary ammonium has been proved to be an excellent cationic passivator, first-principles density functional theory (DFT) computational analyses of the interaction between FAPbI$_3$ and hindered amine-terminated hydrolyzates were performed, and the interface was investigated by means of ab initio Car-Parrinello Molecular Dynamics (CPMD). According to FIGS. 15c and 15d, we first focused on the (100) surface with the iodine vacancy ($V_I$) and tBEDA for defect passivation. The NH group on tBEDA strongly interacted with the Pb of PbI$_6^{2-}$ octahedron through a hydrogen bond (H-bond), and the nitrogen (N) atoms of tBEDA and NH-AS were found to bond with Pb atoms with distances of 2.99 Å and 2.70 Å, respectively, which passivated the interfacial positively charged under-coordinated Pb$^{2+}$ cation. The electron distributions of tBEDA and NH-AS were delocalized after deposition on perovskite, suggesting the localized states of perovskite had been passivated. The calculated density of states (DOS) of the passivated and unpassivated perovskite surfaces (with tBEDA and NH-AS) were plotted. The simulation found that the gap states were almost eliminated after passivation due to the effective charge transfer between the molecule and the perovskite surface.

This work develops a hindered urea bond-based Lewis acid-base (HUBLA) material, which not only passivates as-deposited perovskite film but also releases Lewis bases by absorbing moisture to heal the defects, thereby acting as a "sustained-release medicine" for perovskite. Theoretical calculation supports that the generated Lewis base can effectively coordinate with the unpaired cationic defects. HUBLA also exhibits a strong binding ability that prevents detrimental molecules from penetrating into the grain boundaries. The PSC produces the best PCE of 22.3% and more than 85% of the original efficiency after 3500 hours of storage under ambient conditions. The results prove that the HUBLA has sufficient ability to heal the ionic defects of perovskite and can utilize moisture to realize a long-term stable perovskite device. This is the first demonstration of real-time responsive passivation strategy via the design of DCB, which is fundamentally different from the state-of-the-art technologies and revolutionizes the design of passivation materials, providing new insights into passivation strategies for perovskite electronics.

The subject matter described herein can be used as a dynamic urea bond for the passivator of perovskite solar cell, a hydrolysable and dynamic passivator for perovskite solar cell, and/or a Lewis acid/base-releasable passivator for perovskite solar cell.

EXAMPLES

Unless otherwise indicated in the examples and elsewhere in the specification and claims, all parts and percentages are by weight, all temperatures are in degrees Centigrade, and pressure is at or near atmospheric pressure.

Lead iodide (PbI$_2$, 99.999%) and tin(IV) oxide (SnO$_2$, 15% in H$_2$O colloidal dispersion) were purchased from Alfa Aesar. Triethanolamine (TEA, 98%), tri(ethylene glycol) (TEG, 98%), tert-butylethylenediamine (tBEDA, 98%), 1,3-bis(2-isocyanato-2-propyl)benzene (TMXDI, 97%), cysteamine hydrochloride (98%), lithium bis(trifluoromethanesulfonyl)imide (LiTFSI, 99%), 4-tert-butylpyridine (tBP, 98%) and spiro-OMeTAD (99%), were obtained from Sigma-Aldrich. Dioctyltin dilaurate (96%) was purchased from Merck. Isopropanol (IPA, 99.8%), diethyl ether (99%), N,N-dimethylformamide (DMF, 99.8%), dimethyl sulfoxide (DMSO, 99.8%), chlorobenzene (CB, 99%), acetonitrile (ACN, 99.8%), and 7-butyrolactone (GBL, 99%) were obtained from Acros Organics. 4-Aminobenzotrifluoride (99%) and Poly(3,4-ethylenedioxythiophene) polystyrene sulfonate (PEDOT:PSS) aqueous solution (Al 4083) were purchased from Fluorochem and Heraeus, respectively. Formamidinium iodide (FAI), cesium iodide (CsI), and methylammonium Iodide (MAI) were purchased from Greatcell Solar Materials. Phenyl-C61-butyric acid methyl ester (PCBM) and bathocuproine (BCP) were obtained from Ossila and Lumtec, respectively.

Preparation of Poly(Urea-Urethane) Thermoset.

In a 50 mL three-necked flask, 3.71 gram TMXDI (15.2 mmol) was dissolved in 5 mL DMF and cooled to 4° C. And then 0.86 gram tBEDA (5 mmol) was slowly dropped into the above solution to form oligo-urea. Afterward, 0.188 gram TEA (1.26 mmol), 1.658 gram TEG (8.54 mmol) and two drops of dibutyltin dilaurate were added and the solution was vigorously homogenized. Finally, the polymer solution was charged to a 5×5×0.5 cm$^3$ mould followed by curing at room temperature for 24 hours under nitrogen atmosphere.

Preparation of HUBLA and Characterization.

1.72 gram tBEDA (10 mmol), 10 mL N,N-dimethylformamide were charged in 250 mL three-necked flask under inert nitrogen atmosphere and kept in ice bath. And then 5.37 gram TMXDI was dropped into the solution and stirred for 2 hours. Afterward, 2.5 gram cysteamine hydrochloride and three drops of dioctyltin dilaurate were dissolved in 20 mL DMF and then dropped in the reaction system. The reaction was carried for 3 days and then poured into dried diethyl ether. The precipitates were collected and purified by precipitation at dried diethyl ether for three times, and the white solid was then dried under vacuum overnight. The NMR spectra was performed on a Bruker Avance 400 MHz NMR spectrometer using DMSO-d6 as solvent, while the time-dependent hydrolysis reaction was performed in DMSO-$d_6$/$D_2O$ (0.85/0.15, v/v).

Preparation of Single Crystal $FAPbI_3$.

The $FAPbI_3$ single crystal was synthesized according to the literature. In particular, equimolar FAI and $PbI_2$ were dissolved in GBL with a concentration of 1.5 M. The solution was kept at 100° C. and small $FAPbI_3$ seeds can be obtained within two hours. Afterward, the small $FAPbI_3$ seeds were collected after washed with hot GBL under 100° C. and dried. One small $FAPbI_3$ seed was moved into a fresh solution and heated at 100° C. The small $FAPbI_3$ seed can grow into a larger $FAPbI_3$ crystal within several hours.

Fabrication of Solar Cells.

Indium tin oxide (ITO)-coated glass substrate was cleaned by sequential sonication in deionized water, acetone, and isopropanol, then treating with ultraviolet ozone for 10 min after being dried with an air gun. Following this, $SnO_2$ nanoparticles (2.67%, diluted by deionized water) was spun onto the above substrate at 5,000 rpm for 30 sec., sequentially. And the film was annealed in ambient air at 150° C. for 30 min. For the perovskite deposition, the perovskite precursor solution was prepared according to the literature and optimized. Then the above solution was deposited onto the freshly prepared substrate using a two-step spin-coating method with 1,000 rpm for 10 sec and 5,000 rpm for 20 sec. During the second step, 100 µL of CB was poured on the precursor film 10 sec prior to the end of spin and the film was then annealed at 100° C. for 30 min in a nitrogen-filled glove box. For the target device, HUBLA (0.03-0.2 mg mL$^{-1}$ in IPA) was spun onto the perovskite film. After that, the hole-transporting material (HTM) was deposited onto perovskite film at a spin rate of 4,000 rpm for 30 sec. Here, spiro-OMeTAD was selected as a HTM and dissolved in 1 mL of CB solution which contains 72.3 mg of spiro-OMeTAD, 18 µL of LiTFSI solution (520 mg mL$^{-1}$ in acetonitrile) and 30 µL of 4-tertbutylpyridine. The above film was then left overnight under controlled ambient conditions. Finally, molybdenum(VI) oxide ($MoO_x$) powder and silver (Ag) were thermally evaporated to fabricate the n-i-p cell.

Single-Carrier Device Fabrication.

The hole-only devices were fabricated by the spin-coating method. In particular, PEDOT:PSS was spun onto pre-cleaned ITO substrate at 4,000 rpm for 30 sec, followed by annealed at 140° C. for 30 min. The perovskite precursor solution was subsequently deposited onto the film by using two-step coating method described above. For the target device, HUBLA was then spun atop the perovskite film. Afterward, the devices were completed by thermal evaporation of gold (80 nm) electrode. For the electron-only devices, the perovskite solution was deposited onto the ITO/$SnO_2$ layer by using the above method and then PCBM solution (20 mg mL$^{-1}$ in CB) was spun onto the above film at 4,000 rpm for 30 sec. For the target device, HUBLA was deposited onto the perovskite film. Finally, BCP (5 nm) and Ag (100 nm) layers were subsequently evaporated to fabricate the device.

Photovoltaic Performance Characterization.

The solar cells were measured in a nitrogen-filled glove box with a Keithley 4200 source meter under a simulated AM 1.5 G spectrum and the active area was 0.1 cm$^2$. With a solar simulator (Enli Technology Co., Ltd., Taiwan), the light intensity was calibrated using a KG5 reference cell before each measurement and the J-V curves were taken at a scan rate of 200 mVs$^{-1}$. External quantum efficiency (EQE) measurements were carried out in air by using a QE-R3011 system (Enli Technology Co., Ltd., Taiwan) and the silicon reference cell (KG5) was used for calibration before the start of the measurement for devices. For the solar cell stability test, the unencapsulated solar cells were aged under controlled ambient conditions (relative humidity (RH): ~30%, temperature: ~25° C.). To perform J-V characterization, the samples were taken into a nitrogen-filled glove box and measured at different time intervals.

Space-Charge-Limited Current (SCLC) Characterization.

The SCLC measurement was performed on the hole-only device and electron-only device by using a Keithley 2400 source meter. The I-V curves were taken from 0 to 8 V and scan rate is 1000 mVs$^{-1}$.

Nuclear Magnetic Resonance (NMR) Characterization.

The $^1$H-NMR spectra were recorded using a Bruker Avance 400 MHz NMR spectrometer. Before the start of the measurement, the HUBLA sample was prepared by dissolving in DMSO-$d_6$ solvent. To record the hydrolysis process, the HUBLA sample was also prepared by dissolving in a mixed solvent, where the volume ratio of $D_2O$ to DMSO-d6 is 0.15:1.

Fourier Transform Infrared Spectroscopy (FTIR) Characterization.

The FTIR spectra were taken using a Thermo Scientific Nicolet 6700 FTIR spectrometer, equipped with a diamond attenuated total reflection (ATR) crystal. The ITO/$SnO_2$/perovskite and ITO/$SnO_2$/perovskite/HUBLA samples were measured in ATR mode using spectral range from 4000 cm$^{-1}$ to 400 cm$^{-1}$ and signal average over 32 scans.

Steady-State Photoluminescence (PL) and Time-Resolved Photoluminescence (TRPL) Characterizations.

The PL spectra $FAPbI_3$ and HUBLA-coated $FAPbI_3$ single crystals were recorded using an optical microscope system (UniRAM, Protrustech) with excitation wavelength of 532 nm. The TRPL spectra of $FAPbI_3$ and HUBLA-coated $FAPbI_3$ single crystals were performed on an Edinburgh FLSPP20 Spectrofluorometer and the excitation wavelength is at 405 nm.

Scanning Electron Microscope (SEM) Characterization.

The SEM images of perovskite and target samples were taken with a Hitachi S-800 microscope operated at 15 kV.

X-Ray Diffraction (XRD) Characterization.

The X-ray diffraction patterns of perovskite and target sample were collected on an X-ray powder diffractometer (D8 Discover, Brucker) with CuKα ($\lambda$=1.54059 Å) radiation.

Theoretical Calculation.

The spin theoretical simulations were performed on the Vienna ab initio Simulation Package (VASP, version 5.4.1). The generalized gradient approximation (GGA) with the Perdew-Burke-Emzerhof (PBE) functional form was utilized to evaluate the electron-electron exchange and correlation interactions. The projector augmented-wave (PAW) methods were used to show the core-electron (valence electron) interactions. The kinetic cut-off energy of planewave basis function was set with 400 eV. The force was relaxed below 0.02 eV/Å to optimize the ground-state atomic geometries and the value of the convergence criteria for energy was set with $1.0 \times 10^{-5}$ eV/cell. A Monkhorst-Pack meshes with the size of 3×3×1 were utilized to Brillouin zone for the electronic properties. The stress/force relaxations, total energy, and electronic structures were calculated by Gaussian method. Two layers of $FAPbI_3$ were employed for our simulations, and the bottom layer was fixed and the rest atoms are fully relaxed during geometries optimization. The Adsorption energy ($E_{ads}$) were calculated via following equation:

$$E_{ads}=E_{total}-E_{slab}-E_{Free\ Molecule}$$

where $E_{total}$, $E_{slab}$ and the $E_{Free\ Molecule}$ are total energy of adsorption structures, the energy of clean slab models, and the energy of the free molecules, respectively.

With respect to any figure or numerical range for a given characteristic, a figure or a parameter from one range may be combined with another figure or a parameter from a different range for the same characteristic to generate a numerical range.

Other than in the operating examples, or where otherwise indicated, all numbers, values and/or expressions referring to quantities of ingredients, reaction conditions, etc., used in the specification and claims are to be understood as modified in all instances by the term "about."

While the invention is explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A passivated perovskite structure, comprising:
   a perovskite layer; and
   a hindered urea bond-based Lewis acid-base containing layer adjacent the perovskite layer,
   wherein the hindered urea bond-based Lewis acid-base containing layer comprises a hindered urea bond-based Lewis acid-base having the formula:

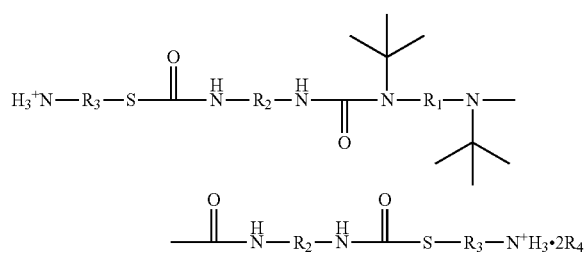

wherein $R_1$ is selected from

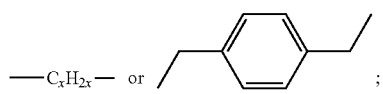

x is selected from 1 to 5; $R_2$ is selected from

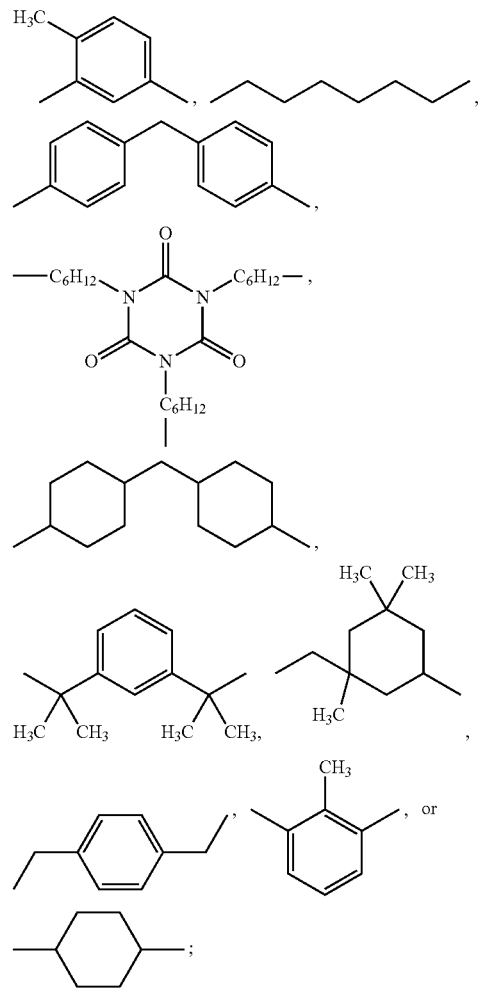

$R_3$ is $-C_xH_{2x}-$, where x is selected from 1 to 5; and $R_4$ is a halide.

2. The passivated perovskite structure according to claim 1, wherein $R_3$ is ethyl and $R_4$ is $Cl^-$.

3. The passivated perovskite structure according to claim 1, wherein the halide is selected from the group of $Cl^-$, $Br^-$, and $I^-$.

4. The passivated perovskite structure according to claim 1, wherein the perovskite layer is sandwiched between two hindered urea bond-based Lewis acid-base containing layers.

5. The passivated perovskite structure according to claim 1, wherein the hindered urea bond-based Lewis acid-base containing layer comprises a hindered urea bond-based Lewis acid-base configured to absorb water and produce a new Lewis base group.

6. The passivated perovskite structure according to claim 1, wherein the hindered urea bond-based Lewis acid-base containing layer has a thickness from 0.1 nm to 25 nm.

7. The passivated perovskite structure according to claim 1, wherein the hindered urea bond-based Lewis acid-base containing layer has a thickness from 0.2 nm to 10 nm.

8. The passivated perovskite structure according to claim 1, wherein the hindered urea bond-based Lewis acid-base containing layer comprises a hindered urea bond-based Lewis acid-base in a concentration of $0.01 \times 10^{-3}$ to $5 \times 10^{-2}$ mg m$^{-2}$.

9. The passivated perovskite structure according to claim 1, wherein the hindered urea bond-based Lewis acid-base containing layer comprises a hindered urea bond-based Lewis acid-base in a concentration of $0.05 \times 10^{-3}$ to $1 \times 10^{-2}$ mg m$^{-2}$.

10. A method of passivating a perovskite layer, comprising:
    forming a hindered urea bond-based Lewis acid-base containing layer adjacent the perovskite layer,
    wherein the hindered urea bond-based Lewis acid-base containing layer comprises a hindered urea bond-based Lewis acid-base having the formula:

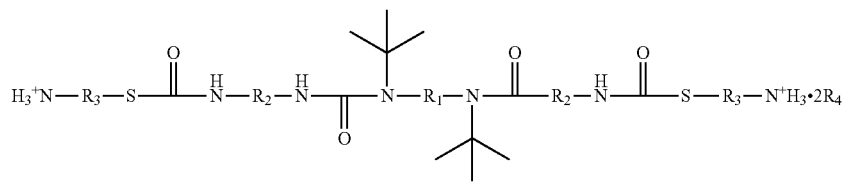

wherein $R_1$ is selected from

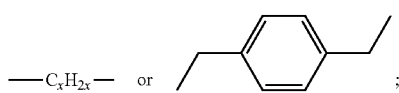

x is selected from 1 to 5; $R_2$ is selected from

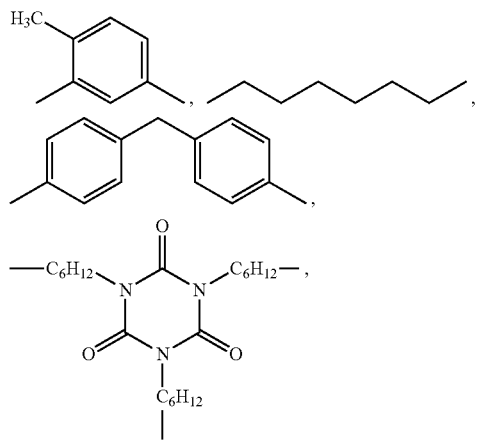

-continued

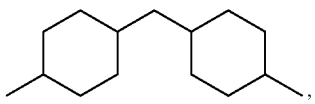

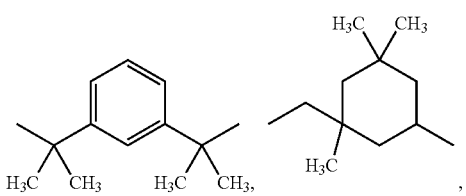

-continued

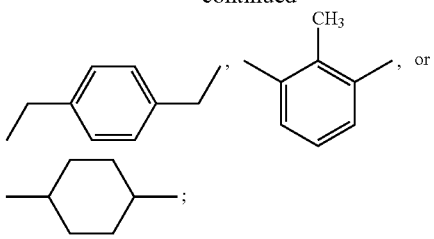

$R_3$ is —$C_xH_{2x}$—, where x is selected from 1 to 5; and $R_4$ is a halide.

11. A perovskite solar cell, comprising:
    a first electrode;
    a hole transport layer adjacent the first electrode;
    a second electrode;
    an electron transfer layer adjacent the second electrode;
    a perovskite layer between the hole transport layer and the electron transfer layer; and
    a hindered urea bond-based Lewis acid-base containing layer adjacent the perovskite layer,
    wherein the hindered urea bond-based Lewis acid-base containing layer comprises a hindered urea bond-based Lewis acid-base having the formula:

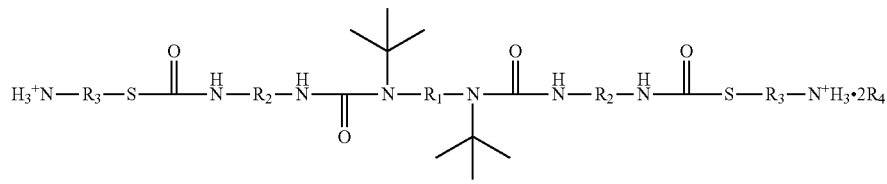

wherein $R_1$ is selected from

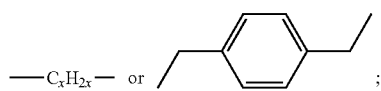

x is selected from 1 to 5; $R_2$ is selected from

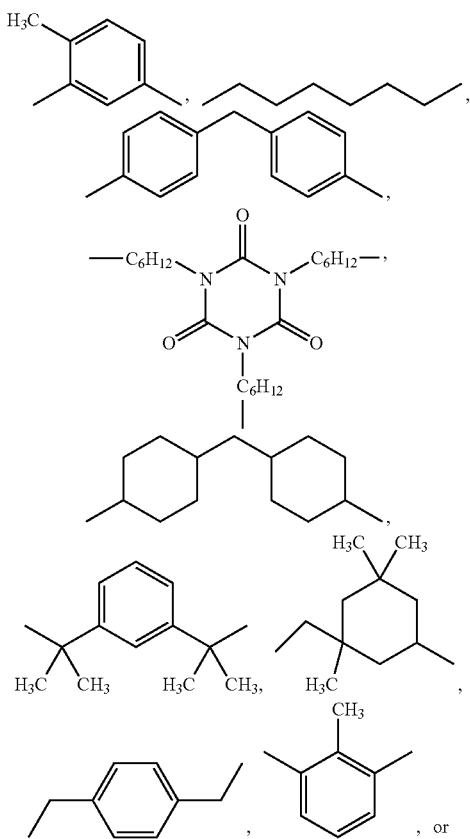

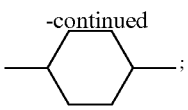

$R_3$ is $-C_xH_{2x}-$, where x is selected from 1 to 5; and $R_4$ is a halide.

12. The perovskite solar cell according to claim 11, further comprising:
    a first hindered urea bond-based Lewis acid-base containing layer between the perovskite layer and the electron transfer layer; and
    a second hindered urea bond-based Lewis acid-base containing layer between the perovskite layer and the hole transport layer.

13. The perovskite solar cell according to claim 11, wherein the hindered urea bond-based Lewis acid-base containing layer has a thickness from 0.1 nm to 25 nm.

14. The perovskite solar cell according to claim 11, wherein the hindered urea bond-based Lewis acid-base containing layer comprises a hindered urea bond-based Lewis acid-base in a concentration of $0.01 \times 10^{-3}$ to $5 \times 10^{-2}$ mg m$^{-2}$.

15. The perovskite solar cell according to claim 11, wherein $R_3$ is ethyl and $R_4$ is Cl$^-$.

16. The perovskite solar cell according to claim 11, wherein the halide is selected from the group of Cl$^-$, Br$^-$, and I$^-$.

17. The perovskite solar cell according to claim 11, wherein the perovskite layer is sandwiched between two hindered urea bond-based Lewis acid-base containing layers.

18. The perovskite solar cell according to claim 11, wherein the hindered urea bond-based Lewis acid-base containing layer comprises a hindered urea bond-based Lewis acid-base configured to absorb water and produce a new Lewis base group.

* * * * *